United States Patent
Okazawa et al.

(10) Patent No.: US 11,606,912 B2
(45) Date of Patent: Mar. 21, 2023

(54) METHOD FOR INCREASING AMOUNT OF PHENOLIC COMPOUND IN PLANT

(71) Applicant: NICHIA CORPORATION, Anan (JP)

(72) Inventors: Atsushi Okazawa, Sakai (JP); Yasuo Fujikawa, Anan (JP); Tomohiro Tsurumoto, Anan (JP)

(73) Assignee: NICHIA CORPORATION, Anan (JP)

(*) Notice: Subject to any disclaimer, the term of this patent is extended or adjusted under 35 U.S.C. 154(b) by 84 days.

(21) Appl. No.: 16/608,756

(22) PCT Filed: Apr. 27, 2018

(86) PCT No.: PCT/JP2018/017259
§ 371 (c)(1),
(2) Date: Oct. 25, 2019

(87) PCT Pub. No.: WO2018/199307
PCT Pub. Date: Nov. 1, 2018

(65) Prior Publication Data
US 2021/0112726 A1   Apr. 22, 2021

(30) Foreign Application Priority Data

Apr. 28, 2017 (JP) .............................. JP2017-090020
Mar. 5, 2018 (JP) .............................. JP2018-038715

(51) Int. Cl.
*A01G 7/04* (2006.01)
*A01H 1/00* (2006.01)

(52) U.S. Cl.
CPC ............. *A01G 7/045* (2013.01); *A01H 1/101* (2021.01)

(58) Field of Classification Search
CPC .......... A01G 7/045; A01H 1/101; A01H 3/02; A01H 3/00; A23B 7/01
See application file for complete search history.

(56) References Cited

U.S. PATENT DOCUMENTS 3,063,195 A * 11/1962 Ravich .................. A01G 9/18
                                                    47/17
3,824,736 A * 7/1974 Davis .................. A01G 7/045
                                                    47/17
(Continued)

FOREIGN PATENT DOCUMENTS

JP      2004-121228 A     4/2004
JP      2008-86272 A      4/2008
(Continued)

OTHER PUBLICATIONS

Apogee Instruments: https://www.apogeeinstruments.com/conversion-ppfd-to-watts/ used for conversion factor.*

(Continued)

*Primary Examiner* — Joshua D Huson
*Assistant Examiner* — Megan J Moroney
(74) *Attorney, Agent, or Firm* — Birch, Stewart, Kolasch & Birch, LLP (57) ABSTRACT

An object of the present invention is to provide a method that can effectively/efficiently increase the amount of a phenolic compound such as a polyphenol. The invention provides a method for increasing an amount of a phenolic compound in a plant, or a method for producing a plant containing an increased amount of a phenolic compound, the method comprising irradiating the/a plant with ultraviolet light, wherein a fluence at wavelengths of 270 to 290 nm is 1500 to 50000 µmol/m² and a fluence at wavelengths of 310 to 400 nm is less than 50% of that at wavelengths of 270 to 290 nm.

16 Claims, 8 Drawing Sheets

(56) References Cited

U.S. PATENT DOCUMENTS

| | | | | |
|---|---|---|---|---|
| 4,788,793 | A * | 12/1988 | Kadkade | A01G 7/045 47/58.1 R |
| 7,774,979 | B2 * | 8/2010 | Hurst | A01H 4/008 47/58.1 LS |
| 9,618,178 | B1 * | 4/2017 | Chappell | F21V 3/02 |
| 10,434,208 | B1 * | 10/2019 | Ngo | H05B 47/19 |
| 10,588,694 | B1 * | 3/2020 | Neev | A61B 18/203 |
| 2008/0298052 | A1 * | 12/2008 | Hurst | A01G 7/045 362/231 |
| 2009/0272029 | A1 * | 11/2009 | Aiking | A61L 2/10 47/1.43 |
| 2011/0016785 | A1 * | 1/2011 | Yamada | H05B 47/16 47/1.01 R |
| 2012/0042419 | A1 * | 2/2012 | Wilson | A01C 1/00 800/298 |
| 2012/0198762 | A1 * | 8/2012 | Lee | A01G 22/00 47/17 |
| 2013/0298445 | A1 | 11/2013 | Aok et al. | |
| 2015/0223402 | A1 * | 8/2015 | Krijn | A01G 7/045 47/58.1 LS |
| 2015/0230409 | A1 * | 8/2015 | Nicole | A01G 7/045 47/17 |
| 2016/0014974 | A1 * | 1/2016 | Grajcar | H05B 45/20 362/230 |
| 2016/0073599 | A1 | 3/2016 | Wargent | |
| 2016/0205739 | A1 * | 7/2016 | Grajcar | H05B 45/20 315/210 |
| 2016/0371830 | A1 * | 12/2016 | Barrasso | G06K 9/00 |
| 2017/0055538 | A1 * | 3/2017 | Ohta | A23L 3/266 |
| 2017/0127622 | A1 * | 5/2017 | Hong | A01G 9/24 |
| 2018/0255709 | A1 * | 9/2018 | Topps | A01G 9/249 |

FOREIGN PATENT DOCUMENTS

| | | | | |
|---|---|---|---|---|
| JP | 2016-7185 A | | 1/2016 | |
| JP | 2016007185 A | * | 1/2016 | |
| WO | WO-2014085626 A1 | * | 6/2014 | A01G 7/045 |
| WO | WO 2018/037281 A1 | | 3/2018 | |

OTHER PUBLICATIONS

Bolton et al., Rethinking the Concepts of Fluence (UV Dose) and Fluence Rate: The Importance of Photon-based Units—A Systemic Review, 2015.*

SI Brochure—9th Edition (2020)—Appendix 3 v1.02, Mar. 2021.*

Seckmeyer et al., A new sunlight simulator for ecological research on plants, 1993.*

International Search Report for PCT/JP2018/017259 (PCT/ISA/210) dated Jun. 19, 2018.

Kusano et al., "Metabolomics reveals comprehensive reprogramming involving two independent metabolic responses of *Arabidopsis* to UV-B light", The Plant Journal, (2011), 67, pp. 354-369.

Written Opinion of the International Searching Authority for PCT/JP2018/017259 (PCT/ISA/237) dated Jun. 19, 2018.

Pan, Plant Physiologies, 6th Ed., 2008, p. 215 (10 pages total w/Partial Translation attached).

* cited by examiner

METHOD FOR INCREASING AMOUNT OF PHENOLIC COMPOUND IN PLANT

TECHNICAL FIELD

The present invention relates to a method for increasing the amount of a phenolic compound in a plant and a method for producing a plant having an increased content of a phenolic compound.

BACKGROUND ART

Phenolic compounds (such as polyphenols) in plants are found to have various bioactivities such as antioxidant, antibacterial and blood pressure elevation inhibitory activities, and therefore have been attracting increasing attention with rising health consciousness.

Thus, techniques have been developed for increasing the amount of a phenolic compound in a plant. Among them, there is a great interest in techniques for increasing the amount of flavonoids in plants by irradiation with ultraviolet light, because plants are believed to synthesize flavonoids having a maximum absorption in the ultraviolet region so as to escape the impacts of ultraviolet light in the sunlight.

For example, Patent Document 1 pertains to a method for increasing the content of a polyphenol in a "harvested" plant by irradiating it with ultraviolet light at the specific wavelengths (of between 240 and 320 nm both inclusive, or of between 300 and 400 nm both inclusive). Patent Document 1 discloses that the appropriate ultraviolet fluence is between 0.5 and 50 J/cm$^2$ (both inclusive) per day and that the wavelength(s) of ultraviolet light to be irradiated to harvested plants should be selected in accordance with the maximum absorption wavelength of a polyphenol of interest.

Patent Document 2 pertains to a method for increasing the content(s) of an ascorbic acid and/or polyphenols in a cultivated monocotyledon (particularly, sprouted Welsh onion) by irradiating it with ultraviolet light at wavelengths of 280 to 380 nm and with a peak at around 312 nm. Patent Document 2 discloses that the appropriate ultraviolet intensity is 0.1 to 1.0 mW·cm$^{-2}$.

Non-Patent Document 1 reports that *Arabidopsis* plants were exposed to narrowband UV-B radiation (280 to 320 nm; peak wavelength: 312 nm; 830 mW/m$^2$/s) continuously for 1 or 4 days to investigate the impacts of UVB stress on the plants and an increase of anthocyanins and flavonols was observed in the plants exposed to ultraviolet for 1 day or more.

CITATION LIST

Patent Literature

Patent Document 1: Japanese Patent Application Publication No. 2004-121228
Patent Document 2: Japanese Patent Application Publication No. 2008-086272

Non-Patent Literature

Non-Patent Document 1: Kusano et al., The Plant Journal, 2011, 67, 354-369

SUMMARY OF INVENTION

Technical Problem

Figure 9:
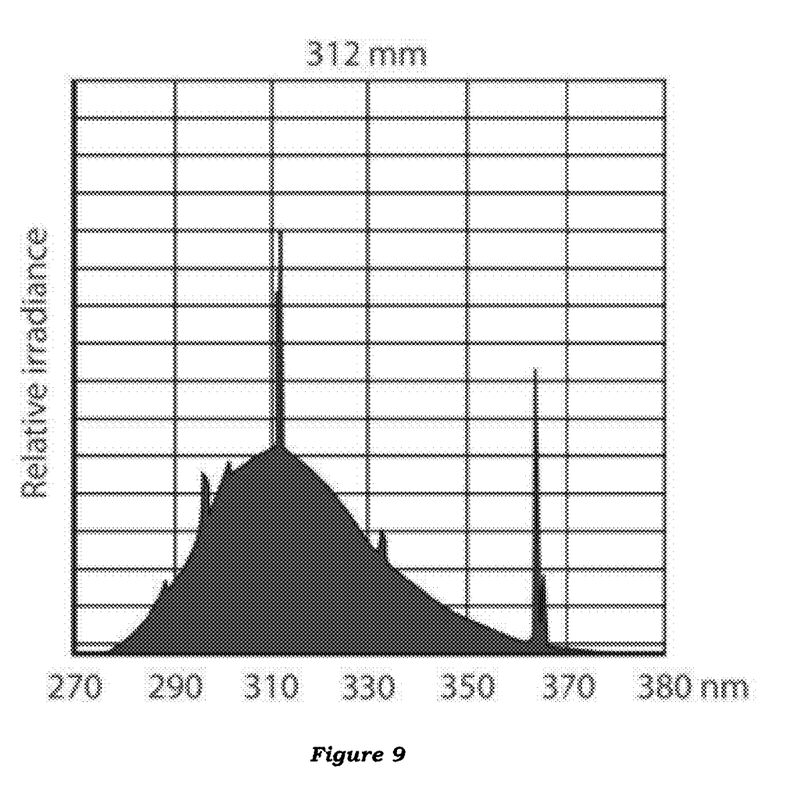
FIG. 9 illustrates the emission spectrum of the ultraviolet lamp (CSL-30B, COSMO BIO) used in Non-Patent Document 1.

As described above, it is known that the exposure of a plant to ultraviolet light (UVA or UVB) increase in the amount of a phenolic compound in the plant. Meanwhile, it is also known that ultraviolet light is harmful to not only plants but organisms in general. The ultraviolet light used in the conventional art has a relatively wide wavelength band, and the emission spectrum of such a UV lamp as used in Non-Patent Document 1 has a peak wavelength at 312 nm but is broad, as illustrated in FIG. 9 for example.

The determination of the exact wavelengths of ultraviolet light contributing to increasing phenolic compounds allows for an efficient increase in the amount of the compounds in plants while reducing the adverse effects caused by exposure to ultraviolet light.

Thus, there is still a need for a method that can effectively/efficiently increase the amount of a phenolic compound such as a polyphenol in a plant.

Solution to Problem

The present inventors investigated the wavelengths and the fluence contributing to increasing phenolic compounds. As a result, the inventors have found that ultraviolet light at specific wavelengths, which are shorter than the conventionally known wavelengths, is effective in increasing phenolic compounds, while conventionally used ultraviolet light includes light at wavelengths that do not contribute to increasing phenolic compounds and, what is worse, can cause a decrease in the abundance of the compounds, thereby completing the present invention.

The invention provides a method for increasing an amount of a phenolic compound in a plant, the method comprising irradiating the plant with ultraviolet light, wherein a fluence at wavelengths of 270 to 290 nm is 1500 to 50000 μmol/m$^2$ and a fluence at wavelengths of 310 to 400 nm is less than 50% of that at wavelengths of 270 to 290 nm.

The invention also provides a method for producing a plant containing an increased amount of a phenolic compound, the method comprising irradiating a plant with ultraviolet light, wherein a fluence at wavelengths of 270 to 290 nm is 1500 to 50000 μmol/m$^2$, while a fluence at wavelengths of 310 to 400 nm is less than 50% of that at wavelength 270 to 290 nm.

The invention also provides a lighting device for use in increasing an amount of a phenolic compound in a plant, the device comprising: a light source capable of emitting light in the wavelength range of 270 to 290 nm wherein an amount of emission at wavelengths of 300 to 400 nm is less than 50% of that at wavelengths of 270 to 290 nm and an amount of emission at wavelengths of 200 nm or more and less than 270 nm is less than 10% of that at wavelengths of 270 to 290 nm, and a control unit to control the light source to provide a fluence at wavelengths of 270 to 290 nm of 1500 to 50000 μmol/m$^2$ at plant level.

Advantageous Effects of Invention

The present invention makes it possible to avoid an adverse effect due to exposure to ultraviolet light that is just harmful, and therefore to increase efficiently an amount of a phenolic compound in a plant, and to produce efficiently a plant containing an increased amounts of a phenolic compound.

DESCRIPTION OF EMBODIMENTS

In an aspect, the invention is a method for increasing an amount of a phenolic compound in a plant, the method comprising irradiating the plant with ultraviolet light, wherein a fluence at wavelengths of 270 to 290 nm is 1500 to 50000 μmol/m² and a fluence at wavelengths of 310 to 400 nm is less than 50% of that at wavelengths of 270 to 290 nm.

In another aspect, the invention is a method for producing a plant containing an increased amount of a phenolic compound, the method comprising irradiating a plant with ultraviolet light, wherein a fluence at wavelengths of 270 to 290 nm is 1500 to 50000 μmol/m², while a fluence at wavelengths of 310 to 400 nm is less than 50% of that at wavelengths of 270 to 290 nm.

As used herein, a numerical range "a to b" ("a" and "b" represent specific numerical values) means the range including both of the values "a" and "b", that is, the range "between a and b (both inclusive)".

The invention is based on new findings that ultraviolet light in the wavelength range of around 270 to 290 nm is effective in increasing the amount of phenolic compounds in plants, while ultraviolet light in the wavelength range of around 310 to 400 nm does not contribute to increasing the amount of phenolic compounds and, what is worse, it can cause an adverse effect, as shown in the Examples below. Thus, according to a method of the invention, one can irradiate a plant with ultraviolet light in a specific wavelength range that is effective in increasing the amount of a phenolic compound in the plant, while avoiding an adverse effect (resulting in a decrease in the abundance of phenolic compounds) due to exposure to ultraviolet light, and therefore increase efficiently the amount of phenolic compound in the plant.

In the present invention, ultraviolet light used is preferably near-ultraviolet light that is less absorbed by the atmosphere than far-ultraviolet light, and is irradiated to a plant in such a way that the fluence at wavelengths of 270 to 290 nm is 1500 to 50000 μmol/m² and the fluence at wavelengths of 310 to 400 nm is less than 50% of that at wavelengths of 270 to 290 nm.

Where the fluence at wavelengths of 270 to 290 nm is less than 1500 μmol/m², a significant increase in the amount of a phenolic compound in a plant may not be achieved, probably because phenolic compounds synthesis is not be significantly activated. Where the fluence at wavelengths of 270 to 290 nm is more than 50000 μmol/m², a plant containing an increased amount of a phenolic compound may not be obtained because of a large damage to the plant. Preferably, the fluence at wavelengths of 270 to 290 nm is 2000 to 40000 μmol/m². With a fluence in this range, a plant containing an increased amount of a phenolic compound may be more efficiently obtained.

Meanwhile, ultraviolet light at wavelengths of 310 to 400 nm does not contribute to an increase in the amount of a phenolic compound in a plant and, what is worse, acts to damage the plant. Therefore, where the fluence at wavelengths of 310 to 400 nm is 50% or more of that at wavelengths of 270 to 290 nm, a plant containing an increased amount of a phenolic compound may not be efficiently obtained. In view of avoiding an adverse effect to a plant, the fluence at wavelengths of 310 to 400 nm is preferably less than 30%, more preferably less than 20%, more preferably less than 10% and the most preferably less than 5%, of that wavelengths of 270 to 290 nm.

In one embodiment, the fluence at wavelengths of 300 to 400 nm is less than 50%, preferably less than 30%, more preferably less than 20% and more preferably less than 10%, of that at wavelengths of 270 to 290 nm. In another embodiment, the fluence at wavelengths of more than 290 nm and 400 nm or less is less than 50%, preferably less than 30%, more preferably less than 20% and more preferably less than 10%, of that at wavelengths of 270 to 290 nm.

Because DNA and RNA have an absorption maximum at around 260 nm, light at wavelengths of 260 nm or less may have a severe adverse effect to plants (such as damaging cells). Therefore, the fluence at wavelengths of 200 to 260 nm is preferably less than 20%, more preferably less than 10%, still more preferably less than 5% and the most preferably less than 1%, of that at wavelengths of 270 to 290 nm.

In one embodiment, the fluence at wavelengths of 200 nm or more and less than 270 nm (preferably at wavelengths of 100 nm or more and less than 270 nm, more preferably at wavelengths of 10 nm or more and less than 270 nm, and still more preferably at wavelengths of 1 nm or more and less than 270 nm) is less than 20%, preferably less than 10%, more preferably less than 5% and the most preferably less than 1%, of that at wavelengths of 270 to 290 nm.

Ultraviolet light in the wavelength range of 270 to 290 nm is irradiated at a photon flux density of, for example, 0.01 to 100 µmol/m$^2$/s. Where the photon flux density is less than 0.01 µmol/m$^2$/s, an increase in the amount of a phenolic compound in a plant may not be efficiently achieved. Where the photon flux density is more than 100 µmol/m$^2$/s, the plant may be damaged quickly. Ultraviolet light in the wavelength range of 270 to 290 nm is preferably irradiated at a photon flux density of 0.1 to 20 µmol/m$^2$/s, and more preferably 1 to 5 µmol/m$^2$/s.

The source of ultraviolet light is not particularly limited as long as it can emit light in the wavelength range of 270 to 290 nm, and may be, for example, any source of ultraviolet light that is commonly used, such as a UV lamp. The UV lamp used is preferably a xenon lamp with a SrSiO3:Pb phosphor for example. Ultraviolet light extracted from the sunlight using an optical filter or the like may be used.

Where the light source used emits light at wavelengths of 310 to 400 nm, 300 to 400 nm, or more than 290 nm and 400 nm or less, in addition to light in the wavelength range of 270 to 290 nm, at a photon flux density of 50% or more of that at wavelengths of 270 to 290 nm, a filter may be used therewith which has a transmittance at wavelengths of 270 to 290 nm higher than that at wavelengths of 310 to 400 nm, 300 to 400 nm, or more than 290 nm and 400 nm or less, respectively. Where the light source emits light at wavelengths of 200 to 260 nm or at wavelengths of less than 270 nm (such as, at wavelengths of 200 nm or more and less than 270 nm, 100 nm or more and less than 270 nm, 10 nm or more and less than 270 nm, or 1 nm or more and less than 270 nm), in addition to light in the wavelength range of 270 to 290 nm, at a photon flux density of 10% or more of that at wavelengths of 270 to 290 nm, a filter may be used therewith which has a transmittance at wavelengths of 270 to 290 nm higher than that at wavelengths of 200 to 260 nm or at wavelengths of less than 270 nm, respectively.

In view of energy efficiency, irradiated light in the wavelength range of 270 to 290 nm has the main peak at, for example, 280±5 nm and more preferably 280±2 nm. It is preferable that no second peak is present or if present, the intensity thereof is 1/10 or less of that of the main peak.

The main peak (within the wavelength range of 270 to 290 nm) preferably has a half-width of 5 to 15 nm. By use of light having a main peak with a half-width of 15 nm or less, one can irradiate a plant with ultraviolet light in a wavelength range that is effective in increasing the amount of a phenolic compound in the plant, while avoiding irradiation with light in a wavelength range that does not contribute to increasing the compound in the plant (and may be just harmful to the plant) (in other words, selective irradiation) and achieve a further increased energy efficiency. It is possible to use light having a main peak with a half-width of less than 5 nm in a method according to the invention. In view of cost efficiency, however, currently it is preferable to use light having a main peak with a half-width of 5 nm or more. In a particular preferable embodiment, ultraviolet light irradiated to a plant has a wavelength spectrum having a peak wavelength at 280±5 nm with a half-width of 5 to 15 nm.

It is particularly preferable that the source of ultraviolet light is a light emitting diode (LED) having a single peak in the emission spectrum. By the use of an LED, one can easily irradiate a plant with ultraviolet light in a wavelength range that is effective in increasing the amount of a phenolic compound in the plant, while avoiding irradiation with light in a wavelength range that does not contribute to increasing the compound in the plant (and may be just harmful to the plant) (in other words, selective irradiation). In view of energy efficiency and economic efficiency, use of an LED is also preferable due to the low heat generation, low power consumption and long life. In addition, the fluence and/or photon flux density can be easily controlled.

An LED capable of emitting ultraviolet light in the wavelength range of 270 to 290 nm may be made of, for example, an AlGaN- or InAlGaN-based material. Specific examples of such LEDs include Deep UV-LED/model: NCSU234BU280 (central wavelength: 280 nm; Nichia Corporation).

The fluence at wavelengths of 270 to 290 nm may be adjusted to 1500 to 50000 µmol/m$^2$ at plant level by, for example, controlling switching on and off the light source (in the case where the plant is placed in a closed space, for example) or by controlling the time required for the plant to pass through the irradiation area (in the case where the plant moves on a conveyor, for example).

In the present specification, the plant is not particularly limited and is preferably a herbaceous plant. The plant may be, for example, an angiosperm, particularly a dicotyledon. Examples of dicotyledons suitable for use in a method according to the invention include plants belonging to the families Brassicaceae (particularly the genera *Brassica* and *Raphanus*), Solanaceae (particularly the genus *Solanum*), Berberidaceae (particularly the genus *Podophyllum*), Theaceae (particularly the genus *Camellia*), Fabaceae (particularly the genus *Glycine*), Rutaceae (particularly the genus *Citrus*), Vitaceae (particularly the genus *Vitis*), Rosaceae (particularly the genus Fragaria), Asteraceae (particularly the genus *Lactuca*) and Lamiaceae (particularly the genus *Perilla*). Specific examples of plants that can be used in the invention include *Arabidopsis thaliana, Podophyllum peltatum, Camellia sinensis, Glycine max, Citrus sudachi, Vitis* spp., *Brassica oleracea* var. *capitata, Brassica oleracea* var. *italica, Brassica rapa* var. *perviridis, Brassica rapa* subsp. *chinensis, Raphanus sativus* var. *longipinnatus, Brassica rapa* subsp. *rapa, Solanum lycopersicum, Solanum melongena, Fragaria* x *ananassa, Lactuca sativa* and *Perilla frutescens* var. *crispa*.

In the present specification, the plant may have the UVR8 photoreceptor.

Without wishing to be bound by theory, it is believed according to the gene expression analysis results mentioned below, that light in the wavelength range of 270 to 290 nm in a plant upregulates, via the UVR8 photoreceptor, the expression of genes for the enzymes and transcription factors involved in the biosynthetic pathways of phenolic compounds (such as phenylpropanoids, flavonoids and anthocyanins), resulting in activation of the biosynthesis.

The plant used in the invention may be a whole plant comprising the shoot (stems and leaves) and root systems, or a part thereof, such as shoot only.

Where the plant is a whole plant, it may be being cultivated or not being cultivated (that is, the plant is under conditions without nutrient supply via the roots). The plant may be cultivated on soil or in soilless system (such as hydroponic cultivation and solid substrate cultivation). Soilless cultivation may be aseptically carried out.

The cultivation may be carried out in a controlled environment. Examples of the environmental conditions to be controlled include light and dark cycle, temperature, humidity, fluence of natural light and/or artificial light, and carbon dioxide concentration. The conditions are not particularly limited as long as they are suitable for cultivation/growth of the plant used.

The light and dark cycle may be selected appropriately according to the plant to be cultivated and its growth stage (for example, a long-day condition of 14 to 18 hours light or a short-day condition of 6 to 10 hours light). The light source of artificial light may be a conventionally used incandescent lamp, fluorescent lamp, white lamp, high-pressure sodium lamp, metal halide lamp, LED or the like. Artificial light may be irradiated at a photosynthetic photon flux density that may be selected appropriately according to the plant to be cultivated, its growth stage and the like. The photosynthetic photon flux density may be, for example, 100 to 500 $\mu mol/m^2/s$.

The temperature may be, for example, 20 to 30° C. and the humidity may be, for example, 50 to 80%.

The carbon dioxide concentration may be, for example, approximately 1000 to 1500 ppm.

The solid/liquid fertilizer(s) may be selected appropriately according to the plant to be cultivated. Generally, the fertilizer contains nitrogen, phosphorus and potassium.

The plant not being cultivated may be kept under natural light, or in a dark place, at a room temperature (such as 15 to 30° C.) or a low temperature (such as 0 to 15° C.).

The plant to be irradiated with ultraviolet light according to the invention may be at any growth stage. In one embodiment, the plant to be irradiated is in the vegetative growth stage and in another embodiment, the plant to be irradiated is not being cultivated (or after harvested (i.e., the plant is a harvest)).

The plant may be a seedling plant or an adult plant. The seedling plant may be a sprout. The sprout is also called a sprouting plant and refers to a seedling plant after germination and before developing a true leaf. The sprout may be obtained by, for example, culture in the dark at a temperature of 20 to 25° C. for 7 to 10 days.

Where the plant is being cultivated, ultraviolet light irradiation according to the invention may be performed in either a light phase or a dark phase.

A method according to the invention may further comprise placing the plant in the dark for 12 hours or more after irradiation of light in the wavelength range of 270 to 290 nm (ultraviolet light). As used herein, "placing in the dark" refers to placing the plant in a dark place or a dark room (where the photosynthetic photon flux density does not cause photosynthesis in the plant, more specifically, the photosynthetic photon flux density 10 $\mu mol/m^2/s$). The time for placing the plant in the dark is preferably 24 hours or more, more preferably 36 hours or more, still more preferably 48 hours or more and yet more preferably 72 hours or more. The upper limit of the time for placing the plant in the dark is not particularly limited as long as the content of a phenolic compound in the plant is increased as compared to the plant without irradiation, and may be, for example, 300 hours and more specifically 288 hours (or less).

For example, the plant may be placed in the dark at a room temperature or a low temperature.

The amount (content) of a phenolic compound in a plant is further increased by placing it in the dark for 12 hours or more after ultraviolet light irradiation.

In the present specification, the phenolic compound is not particularly limited as long as it can be naturally synthesized in the plant used, and may be, for example, a phenylpropanoid or a polyphenol. Examples of polyphenols include flavonoids, tannins and lignans. Examples of flavonoids include anthocyanins, flavans (such as catechins), flavones, isoflavones and flavonols.

Anthocyanins are glycosides where anthocyanidins bound to a sugar moiety (such as glucose, galactose or rhamnose). Examples of anthocyanidins that are commonly found in plants include pelargonidin, cyanidin, peonidin, delphinidin, petunidin and malvidin. Anthocyanins are pigments widely present in the plant kingdom, which produce colors ranging from red to purple to blue, used as plant-based colorants (e.g. for food products) and are known to be antioxidants. Therefore, an anthocyanin is a preferable phenolic compound which is sought to be increased in a plant according to the present invention.

An example of anthocyanins in, for example, *A. thaliana* is represented by the following chemical formula:

In the formula, an anthocyanidin moiety, a peonidin moiety in this case, is surrounded by the line.

The expressions "increasing the amount of a phenolic compound", "increasing the content of a phenolic compound" and the like as used herein refer to an increase in the amount of a phenolic compound by, for example, 10% or more, preferably 20% or more, more preferably 50% or more and still more preferably 100% or more, as compared to a plant without ultraviolet light irradiation according to the invention. The expressions "increasing the amount of a phenolic compound", "increasing the content of a phenolic compound" and the like also refers to a novel synthesis, after irradiation, of a phenolic compound that was not synthesized before irradiation.

The phenolic compound may be quantified by any of the known techniques, for example, chromatography. Examples of chromatography include liquid chromatography (such as HPLC). The liquid chromatography may be reverse phase chromatography.

By ultraviolet light irradiation according to the invention, a plant can be produced wherein the amount of a phenolic compound is 1.1 times or more, preferably 1.2 times or more, more preferably 1.5 times or more, more preferably 2 times or more, e.g., 3 times or more, of that of a non-irradiated plant. Thus, according to a method of the invention, the plant produced can be inexpensively provided as a high-value-added food.

The plant produced according to a method of the invention is a suitable raw material for production of the phenolic compound of which content is increased in the plant.

Thus, the present invention also provides a method for producing a phenolic compound, the method comprising:

a step of irradiating a plant with ultraviolet light, wherein a fluence at wavelengths of 270 to 290 nm is 1500 to 50000 µmol/m$^2$, while a fluence at wavelengths of 310 to 400 nm is less than 50% of that at wavelengths of 270 to 290 nm; and a step of obtaining the phenolic compound from the plant.

The invention also provides a method for producing a phenolic compound, the method comprising:

a step of irradiating a plant with ultraviolet light, wherein a fluence at wavelengths of 270 to 290 nm is 1500 to 50000 µmol/m$^2$, while a fluence at wavelengths of 300 to 400 nm is less than 50% of that at wavelengths of 270 to 290 nm and a fluence at wavelengths of 200 nm or more and less than 270 nm is less than 10% of that at wavelengths of 270 to 290 nm; and a step of obtaining the phenolic compound from the plant.

The step of obtaining the phenolic compound from the plant may be performed by, for example, extraction. The extraction may be carried out by any of the known techniques, such as solvent extraction or supercritical extraction.

The solvent used in solvent extraction may be appropriately selected from the known solvents. The solvent used is, for example, water (from room temperature water to boiling water) or a water-miscible organic solvent, or a mixed solvent thereof (a mixed solvent of water and one or more water-miscible organic solvents, a mixed solvent of two or more water-miscible organic solvents). The water-miscible organic solvent may be a polar organic solvent, including, for example, methanol, ethanol, n- or iso-propanol, acetonitrile, acetone, dioxane, ethyl acetate, dimethyl sulfoxide, dimethylformamide, ethylene glycol or tetrahydrofuran. Water used may be hot water or boiling water.

Extraction may be carried out under heating (such as 80 to 90° C.) and/or increased pressure. Extraction may be reflux extraction. The extraction time is not particularly limited and may be determined appropriately in view of extraction efficiency.

For extraction, the leaves and/or the stems of the plant may be used but preferably the whole of the plant is used, regardless of the growth stage. The plant may be subjected to extraction as it is or after grinding. Before extraction or grinding, the plant may be dried and/or frozen.

An extract may be filtered with an appropriate filter or centrifuged to remove contaminants, for example.

Where the phenolic compound of interest is an anthocyanin, a polar organic solvent, for example, may be used for extraction. The polar organic solvent may contain an acid added thereto. The acid may be, for example, hydrochloric acid, sulfuric acid, formic acid, acetic acid, phosphoric acid, trichloroacetic acid, trifluoroacetic acid or perchloric acid. The organic solvent may contain the acid at a weight ratio of, for example, 0.1 to 10% and preferably 1 to 3%. Specific examples of extractants include a mixed solvent of trifluoroacetic acid, formic acid or acetic acid/methanol, a mixed solvent of acetone/methanol/formic acid or acetic acid, and a mixed solvent of hydrochloric acid/methanol.

From the extract obtained, the phenolic compound may be purified.

Purification may be performed by, for example, chromatography. The chromatography may be, for example, column chromatography (particularly HPLC) and is preferably performed in a reverse phase mode.

The column used in column chromatography may be appropriately selected from the known columns according to the separation mode. The column used in reverse phase chromatography is commonly, but not limited to, an octadecyl silica gel (ODS) column (also referred to as C18 column). A C30 column, for example, may also be used.

For chromatography, an eluent used may be water or a polar organic solvent, or a mixed solvent thereof (a mixed solvent of water and one or more polar organic solvents, a mixed solvent of two or more polar organic solvents). The polar organic solvent is as described above. The eluent may contain an acid such as trifluoroacetic acid, formic acid, acetic acid, phosphoric acid or trichloroacetic acid at, for example, 0.01 to 10 M.

Chromatography may be performed in a gradient mode. The gradient mode chromatography may be carried out with eluent A being a mixed solvent of a polar solvent and water (at mixing ratio of, for example, 0:100 to 10:90), optionally containing 0.01 to 10 M of an acid, and eluent B being a mixed polar solvent (at mixing ratio of, for example, 50:50) or a mixed solvent of a polar solvent and water (at mixing ratio of, for example, 50:50 to 100:0), optionally containing 0.01 to 10 M of an acid, and a gradient from 100:0 to 0:100 (A:B) in 30 to 60 minutes, for example.

The flow rate is not particularly limited and may be, for example, 0.2 to 2 ml/min.

The phenolic compound may be detected by measuring an absorbance at, for example, 250 to 300 nm. An anthocyanin can be detected by measuring an absorbance at 500 to 550 nm.

The phenolic compound produced by a method according to the invention can be used as a raw material for a functional food (a food for specified health uses, or a food with nutrient function claims), a medicament or any other industrial product. Thus, according to a method of the invention, the phenolic compound produced can be inexpensively provided as a raw material for a functional food, a medicament or any other industrial product.

In one embodiment, the plant is *Arabidopsis thaliana*. *A. thaliana* develops in a relatively short period of time and is easy to grow, and therefore is suitable for production of a phenolic compound (such as an anthocyanin) according to a method of the invention.

The invention also relates to a lighting device for use in increasing an amount of a phenolic compound in a plant, the device comprising: a light source capable of emitting light in the wavelength range of 270 to 290 nm wherein an amount of emission at wavelengths of 300 to 400 nm is less than 50% of that at wavelengths of 270 to 290 nm and an amount of emission at wavelengths of 200 nm or more and less than 270 nm is less than 10% of that at wavelengths of 270 to 290 nm; and a control unit to control the light source to provide a fluence at wavelengths of 270 to 290 nm of 1500 to 50000 µmol/m$^2$ at plant level.

The lighting device according to the invention is useful in the methods according to the invention for increasing an amount of a phenolic compound in a plant, for producing a plant containing an increased amount of a phenolic compound, and for producing a phenolic compound (collectively referred to as "the methods according to the invention").

The light source is as described above for the methods according to the invention.

Preferably, the light source emits light at a fluence at wavelengths of 200 nm or more and less than 270 nm (more preferably 100 nm or more and less than 270 nm, more preferably 10 nm or more and less than 270 nm, and still more preferably 1 nm or more and less than 270 nm) of less than 5%, and more preferably of less than 1%, of that at wavelengths of 270 to 290 nm.

The light source also preferably emits light at a fluence at wavelengths of 300 to 400 nm of less than 30%, more preferably of less than 20%, and still more preferably of less than 10%, of that at wavelengths of 270 to 290 nm. In one specific embodiment, the light source emits light at a fluence at wavelengths of more than 290 nm and 400 nm or less of less than 50%, preferably less than 30%, more preferably less than 20%, and more preferably less than 10%, of that at wavelengths of 270 to 290 nm.

In this regard, specific preferable examples of the light source include an LED, and a xenon lamp (a xenon lamp with a SrSiO3:Pb phosphor, for example), equipped with a filter required (see above), and an LED is more preferred.

The lighting device according to the invention may comprise only one light source, or more than one light source.

The control unit controls the timing of switching on and off the light source and/or the dimming of the light source. The control unit may be, for example, a timer and/or a pulse width modulation circuit.

The lighting device according to the invention may be situated in a closed space for cultivating and/or storing a plant. The closed space is not limited with regard to the shape and size thereof as long as it is possible to cultivate and/or store a plant therein, and may be, for example, a plant cultivation facility, a plant factory, a storehouse, a container, a refrigerator or the like.

In the closed space, the lighting device may be situated above, and/or lateral to, and/or below, the plant.

In the closed space, an air-conditioning system may be provided to adjust the inner temperature and/or humidity to predetermined values.

In one preferable embodiment, the photosynthetic photon flux density in the closed space may be maintained at 10 µmol/m$^2$/s or less (meaning that the closed space is a "dark place" or "dark room") for 12 hours or more after the fluence of light at wavelengths of 270 to 290 nm from the lighting device reaches 1500 to 50000 µmol/m$^2$. More preferably, the dark condition is maintained for 24 hours or more, more preferably 36 hours or more, more preferably 48 hours or more, and still more preferably 72 hours or more. The upper limit of the darkness period is not particularly limited as long as the content of a phenolic compound in the plant is increased as compared to a non-UV irradiated plant, and may be, for example, 300 hours or 288 hours (or less).

EXAMPLES (Experiment 1)

Plants (*Arabidopsis thaliana*) were grown vegetatively on MS (Murashige-Skoog) agar medium under aseptic conditions. Specifically, the sterilized seeds were inoculated on MS agar medium and grown for 14 days after inoculation at a temperature of 22 to 23° C. in a plant incubator (BMS-PS08RGB2, Bio Medical Science K.K.) under long-day conditions (16 hours light/8 hours dark; photosynthesis effective photon flux density: 200 µmol/m$^2$/s).

Figure 1:
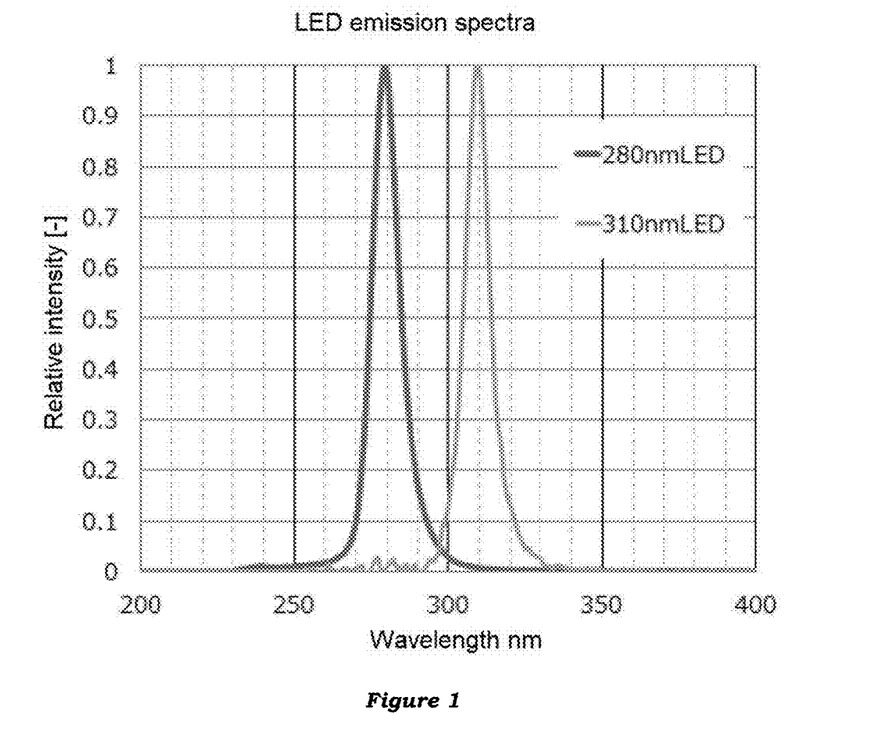
FIG. 1 illustrates the emission spectra of the ultraviolet LEDs used in the Examples (Experiment 1).

After 14-day growing, the plants were irradiated with ultraviolet light from an LED, having a peak wavelength at 280 nm (half-width 10 nm; Deep UV-LED/model: NCSU234BU280) or at 310 nm (half-width 10 nm; Deep UV-LED/model: NCSU234BU310) at an irradiance (fluence rate) of 2.5 µmol photons/m$^2$/s for continuous 15 minutes, 4 hours or 4 days (total number of photons: 2250, 36000 and 864000 µmol/m$^2$). The emission spectra of the LEDs used are illustrated in FIG. 1.

Then, the plants were placed in a dark place before determination of anthocyanins. Plants served as control were placed in a dark place for 24 hours without ultraviolet light irradiation.

Twenty-four hours after ultraviolet light irradiation, the plants (dry weight: approximately 30 mg) were freeze-crushed and subjected to solvent extraction with 80% methanol.

Figure 2:
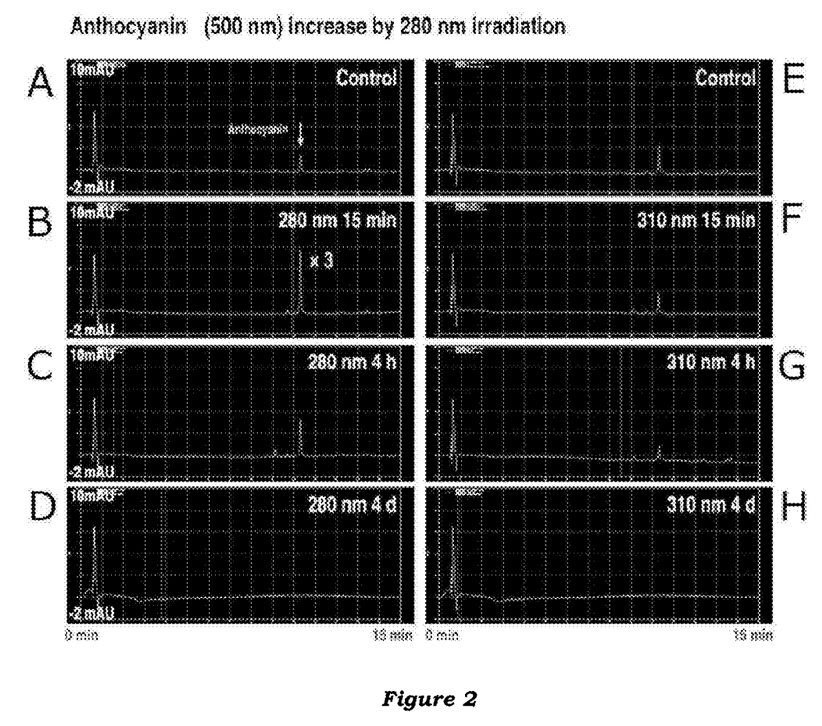
FIG. 2 illustrates HPLC chromatograms (detection at 500 nm) indicating the amount of anthocyanins in the plants (*Arabidopsis thaliana*) irradiated with ultraviolet light in Experiment 1. Ultraviolet light irradiated had a peak wavelength at 280 nm (B to D) or 310 nm (F to H), and the irradiation time was 15 minutes (B, F), 4 hours (C, G), or 4 days (D, H). A and E are from non-UV-irradiated controls.

The amount of anthocyanins in the extracts obtained was analyzed by high performance liquid chromatography (LC-10, Shimadzu Corporation) under the following conditions:

HPLC Conditions:
 Column: ODS column (Kinetex 5 u C18 100 A, Phenomenex)
 Column temperature: 40° C.
 Flow rate: 2 ml/min
 Injection: 10 µl
 Mobile phase:
  Eluent A: 0.1% formic acid aqueous solution
  Eluent B: 0.1% formic acid in acetonitrile
  Linear gradient: 1% to 99% B in 49 minutes
 Detection: 210 to 750 nm The results are shown in FIG. 2.

The amount of anthocyanins (peak height) was increased in the plants irradiated with ultraviolet light having a peak wavelength at 280 nm for 15 minutes or 4 hours, by 3 times or more (B), or almost 2 times (C), respectively, than that of controls (A). No anthocyanins were detected in the plants irradiated for 4 days (D).

In all the plants irradiated with ultraviolet light having a peak wavelength at 310 nm for 15 minutes, 4 hours or 4 days (F to H), the amount of anthocyanins was decreased relative to that of controls (E).

The results demonstrate that irradiation with ultraviolet light at wavelengths of around 280 nm is effective in increasing the amount of anthocyanins in *A. thaliana*, while irradiation with ultraviolet light at wavelengths of around 310 nm does not contribute to the increase and, what is worse, it can cause some negative effects resulting in a decrease in the amount of anthocyanins.

(Experiment 2)

Figure 3:
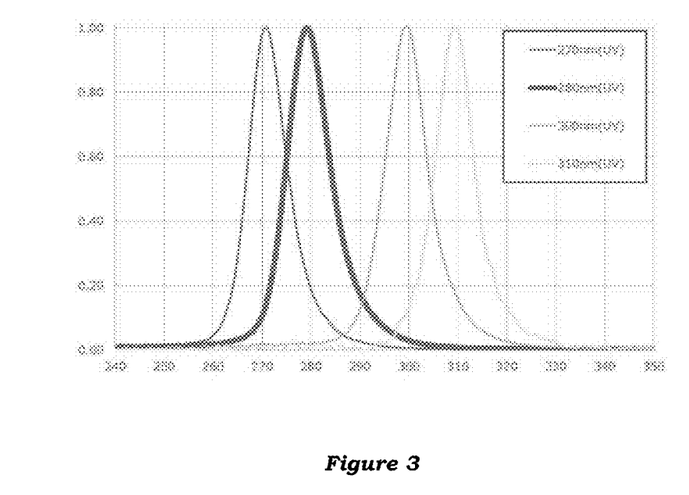
FIG. 3 illustrates the emission spectra of the ultraviolet LEDs used in the Examples (Experiment 2). The emission spectra with peak wavelengths at 280 and 310 nm are of the LEDs used in Experiment 1.

The experiment was carried out as in Experiment 1, except that the LED used had a peak wavelength at 270 nm (half-width 10 nm; Deep UV-LED/model: NCU234BU270) or at 300 nm (half-width 10 nm; Deep UV-LED/model: NCU234BU300) and the irradiation time was 15 minutes for 270 nm irradiation (total number of photons: 2250 µmol/m$^2$) and 15 minutes or 4 hours for 300 nm irradiation (total number of photons: 2250 and 36000 µmol/m$^2$, respectively). The emission spectra of the LEDs used are illustrated in FIG. 3. For comparison, the spectra of the LEDs for 280 and 310 nm irradiations are also illustrated in the figure.

Figure 4:
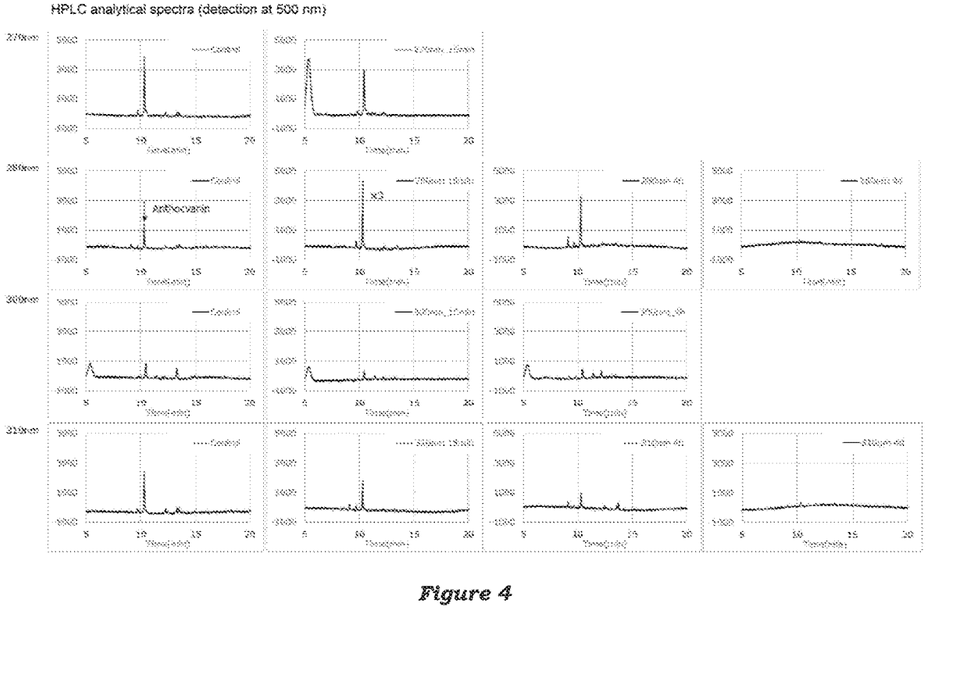
FIG. 4 illustrates HPLC chromatograms (detection at 500 nm) indicating the amount of phenolic compounds in the plants (*Arabidopsis thaliana*) irradiated with ultraviolet light in the Examples (Experiment 2). The wavelengths indicated on the left are the peak wavelengths of ultraviolet light irradiated. The irradiation time was 0 (i.e., non-UV-irradiated controls; the leftmost column), 15 minutes (the $2^{nd}$ column from the left), 4 hours (the 3rd column from the left) or 4 days (the rightmost column). The results obtained with light having a peak wavelength at 280 nm and with light having a peak wavelength at 310 nm are from Experiment 1.

The results are shown in FIG. 4. For comparison, the results from Experiment 1 are also shown in the figure.

In the plants irradiated with ultraviolet light having a peak wavelength at 270 nm for 15 minutes or ultraviolet light having a peak wavelength at 300 nm for 15 minutes or 4 hours, the amount (peak height) of anthocyanins was decreased than that of controls.

The results demonstrate that neither of irradiations with ultraviolet light at wavelengths of less than 270 nm or of around 300 nm contributes to increasing the amount of anthocyanins in *A. thaliana* and causes some negative effects resulting in a decrease in the amount of anthocyanins.

The wavelength composition of light from the LEDs used in Experiments 1 and 2 are indicated below.

TABLE 1

|  | Peak wavelength (nm) | | | |
| --- | --- | --- | --- | --- |
|  | 270 | 280 | 300 | 310 |
| 270-290 nm | 64.3% | 86.5% | 5.4% | 1.3% |
| More than 290 nm | 2.8% | 8.6% | 92.8% | 98.3% |
| Less than 270 nm | 33.0% | 5.0% | 1.8% | 0.3% |

(Experiment 3)

Harvested or purchased, sudachi plants (*Citrus sudachi*, pericarps), mayapple plants (*Podophyllum peltatum*, roots), tea plants (*Camellia sinensis*, leaves) and soybean plants (*Glycine max*, pericarps) were irradiated with ultraviolet light having a peak wavelength at 280 nm (half-width 10 nm) at an irradiance of 5 μmol photons/$m^2$/s for continuous 15 minutes (total number of photons: 4500 μmol/$m^2$) using an LED (Deep UV-LED/model: NCSU234BU280). The leaves and stems were irradiated with ultraviolet light while being immersed in shallow pure water to prevent them from drying and ageing.

Then, the plants were placed in a dark place before determination of phenolic compounds. Plants served as control were placed in a dark place for 24 hours without ultraviolet light irradiation. The leaves and stems were placed in the dark while being immersed in shallow pure water to prevent them from drying and ageing.

Twenty-four hours after ultraviolet light irradiation, the plant parts (dry weight: approximately 30 mg) were freeze-crushed and subjected to solvent extraction with 80% methanol.

Figure 5:
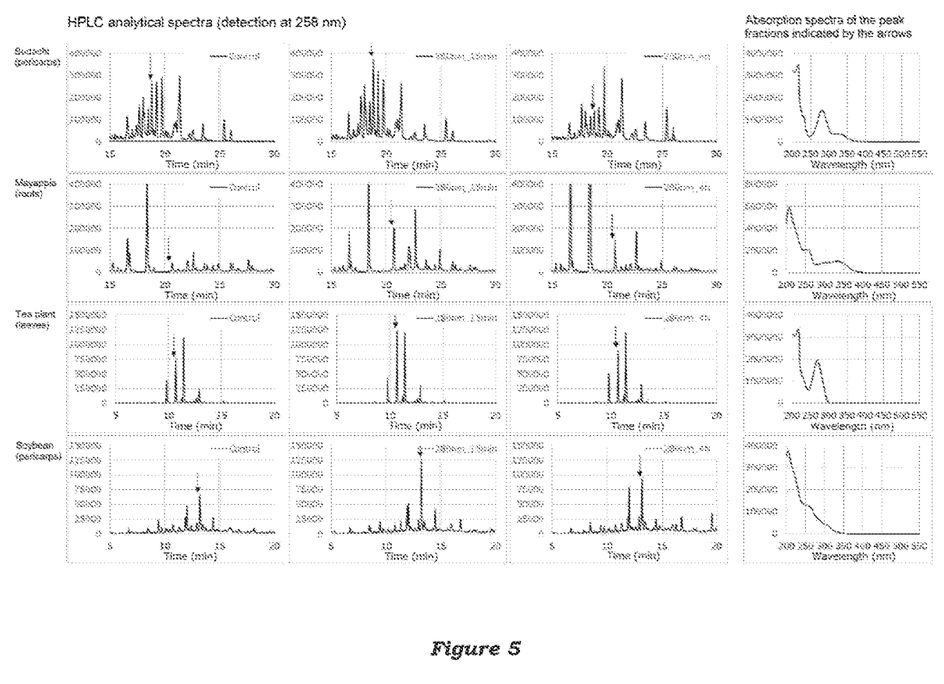
FIG. 5 illustrates HPLC chromatograms (detection at 258 nm) indicating the amount of phenolic compounds in the plants (*Citrus sudachi* (pericarps), *Podophyllum peltatum* (roots), *Camellia sinensis* (leaves) and *Glycine max* (pericarps)) irradiated with ultraviolet light in the Examples (Experiment 3). Ultraviolet light irradiated had a peak wavelength at 280 nm, and the irradiation time was 0 (i.e., non-UV-irradiated controls; the leftmost column), 15 minutes (the $2^{nd}$ column from the left) or 4 hours (the $3^{rd}$ column from the left). The rightmost column includes absorption spectra of the peak fractions indicated with arrows.

The amount of phenolic compounds in the extracts obtained was analyzed by high performance liquid chromatography (Prominence, Shimadzu Corporation) under the following conditions:

HPLC Conditions:
Column: ODS column (Triart C18 (150×4.6 mm, S-5 μm), YMC)
Column temperature: 40° C.
Flow rate: 1 ml/min
Injection: 10 μl
Mobile phase:
Eluent A: 0.1% formic acid aqueous solution
Eluent B: 0.1% formic acid in acetonitrile
Linear gradient: 1% to 100% B in 30 minutes
Detection: 190 to 800 nm
The results are shown in FIG. 5.

In the extracts from sudachi plants (pericarps), mayapple plants (roots), tea plants (leaves) and soybean plants (pericarps) irradiated with ultraviolet light having a peak wavelength at 280 nm for 15 minutes or 4 hours, increased absorption peaks were observed at around 250 to 300 nm. The absorption peaks are characteristic to phenolic compounds.

The results demonstrate that irradiation with ultraviolet light at wavelengths of around 280 nm is effective in increasing the amount of phenolic compounds in sudachi, mayapple, tea and soybean plants.

(Experiment 4)

Purchased grape berries (pericarps) were irradiated with ultraviolet light having a peak wavelength at 280 nm (half-width 10 nm) at an irradiance of 2.5 μmol photons/$m^2$/s for continuous 15 minutes or 4 hours (total number of photons: 2250 or 36000 μmol/$m^2$, respectively) using a LED (Deep UV-LED/model: NCSU234BU280). The berries were then placed in a dark place before determination of phenolic compounds. Plants served as control were placed in the dark for 24 hours without ultraviolet light irradiation.

Twenty-four hours after ultraviolet light irradiation, the pericarps (dry weight: approximately 40 to 100 mg) were freeze-crushed and subjected to solvent extraction with 80% methanol. The amount of phenolic compounds in the extracts obtained was analyzed by high performance liquid chromatography (Prominence, Shimadzu Corporation) under the same conditions as in Experiment 3.

Figure 6:
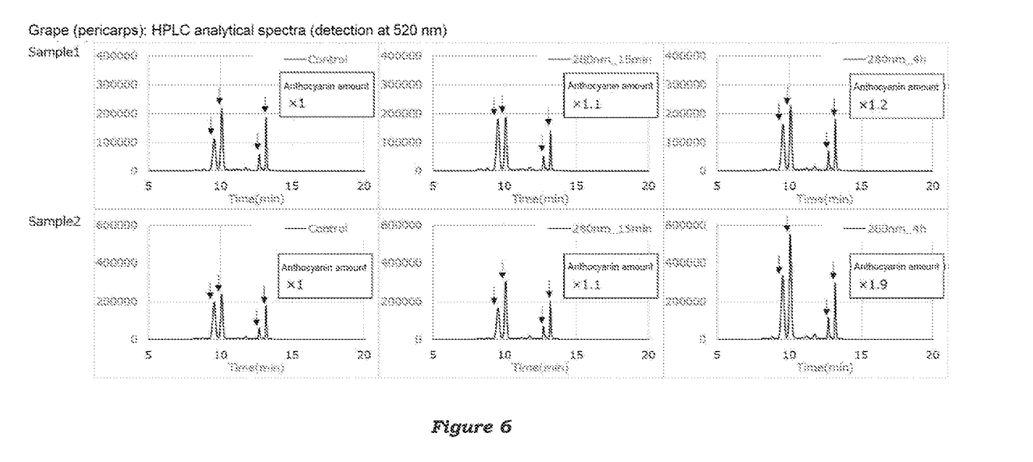
FIG. 6 illustrates HPLC chromatograms (detection at 520 nm) indicating the amount of anthocyanins in grape plants (pericarps) irradiated with ultraviolet light in the Examples (Experiment 4). Ultraviolet light irradiated had a peak wavelength at 280 nm, and the irradiation time was 0 (i.e., non-UV-irradiated controls; the leftmost column), 15 minutes (the $2^{nd}$ column from the left) or 4 hours (the rightmost column).

The results are shown in FIG. 6.

In the extracts from grape plants (pericarps) irradiated with ultraviolet light having a peak wavelength at 280 nm for 15 minutes or 4 hours, it was observed that total absorption peak areas at wavelengths of around 520 nm, characteristic to anthocyanins, were increased (1.2 to 1.9 times relative to that of the non-irradiated controls).

The results demonstrate that irradiation with ultraviolet light at wavelength around 280 nm is effective in a further increase of anthocyanins in grape plant, which contains a high level of anthocyanins even before irradiation.

(Experiment 5)

Plants (*A. thaliana*) were irradiated with ultraviolet light having a peak wavelength at 280 nm for continuous 15 minutes (total number of photons: 2250 μmol/$m^2$), according to the method described in Experiment 1, Then, the plants were placed in a dark place for 12, 24, 48, 72, 96 or 288 hours before determination of anthocyanins.

After placing in the dark, the plants (dry weight: approximately 30 mg) were freeze-crushed and subjected to solvent extraction with 80% methanol.

The amount of anthocyanins in the extracts obtained was analyzed according to the method described in Experiment 1.

Figure 7:
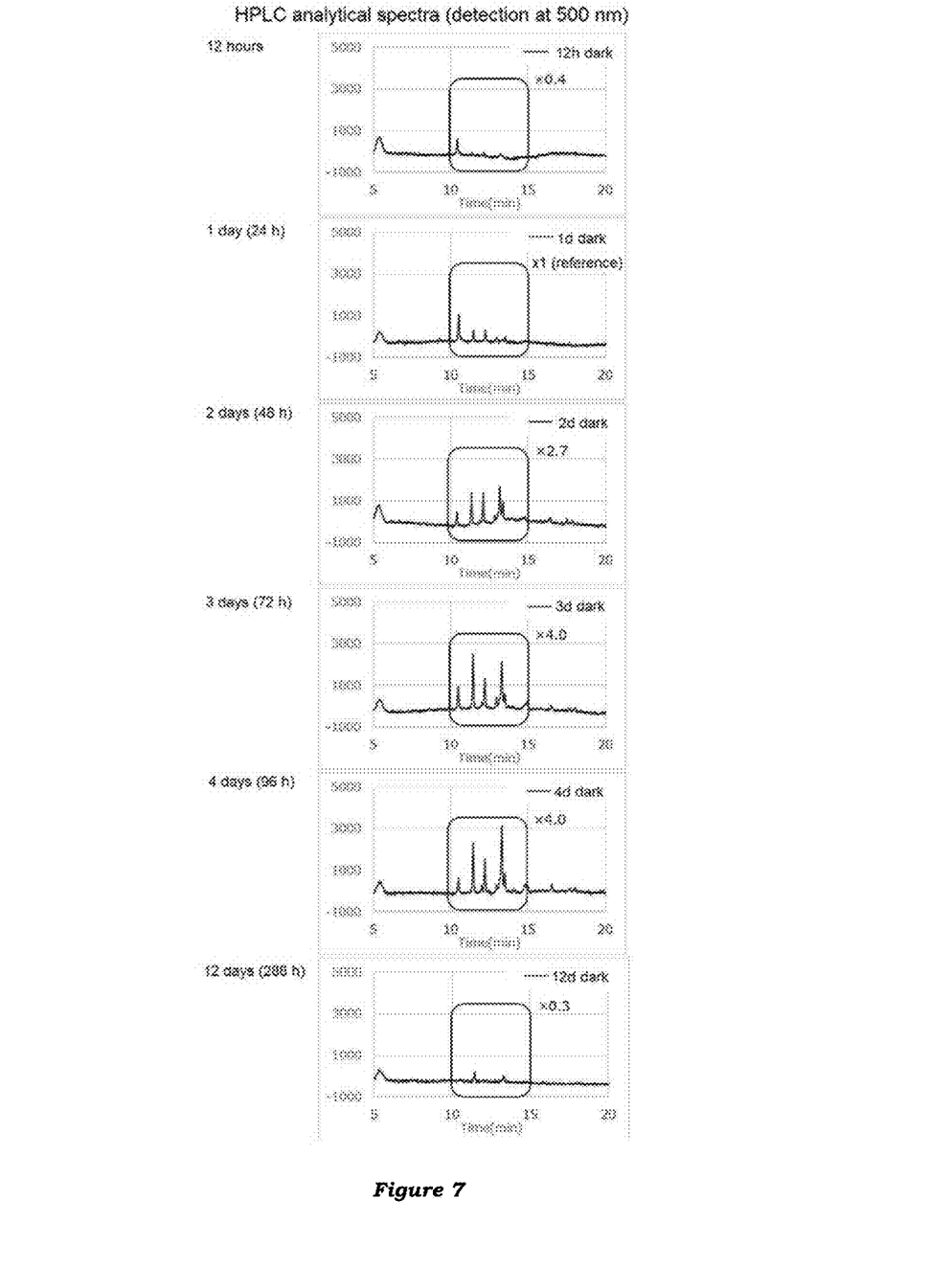
FIG. 7 illustrates HPLC chromatograms (detection at 500 nm) indicating the amount of anthocyanins in plants (*A. thaliana*) that were irradiated with ultraviolet light and then left in the dark for 12, 24, 48, 72, 92 or 288 hours in the Examples (Experiment 5). Ultraviolet light irradiated had a peak wavelength at 280 nm and the irradiation time was 15 minutes.

The results are shown in FIG. 7. The magnifications (expressed as "×0.4" and "×4.0", for example) indicated in the figure are relative to the level (reference values) in the plants placed in the dark for 24 hours after ultraviolet light irradiation. It should be noted that in the plants placed in the dark for 24 hours after ultraviolet light irradiation, the amount of anthocyanins is 3 times than that of the non-irradiated controls [see FIG. 1]. This means that "0.4 times" and "4 times" relative to the level in the plants placed in the dark for 24 hours after ultraviolet light irradiation correspond to "1.2 times" and "12 times", respectively, than that of the non-irradiated controls.

The results demonstrate that the amount of phenol compounds in the ultraviolet light-irradiated plants is further increased by placing them in the dark for 24 hours or more after ultraviolet light irradiation.

(Experiment 6)

Gene Expression Analysis

Preparation of Total RNA

Total RNAs were prepared from plants (*A. thaliana*) irradiated with ultraviolet light having a peak wavelength at 280 nm (half-width 10 nm; Deep UV-LED/model: NCSU234BU280) for 45 minutes, immediately after irradiation using the RNeasy mini kit (Qiagen) according to the Manufacturer's instructions.

Expression Analysis

The total RNAs prepared were subjected to RNA-seq analysis (Takara Bio Inc.). Sequence analysis was carried out with the HiSeq 2500 system (Illumina, Inc.) and the reference sequence was from the TAIR 10.37.

Table 2 shows the genes with two-fold or more increased expression level (FPKM; Fragments Per Kilobase of exon per Million mapped reads).

TABLE 2

Gene expression analysis data
Genes whose expression levels are increased 2-fold or more by irradiation with ultraviolet light (peak wavelength 280 nm)

| Gene name | Name | Log2 FPKM value | | Note |
|---|---|---|---|---|
| | | Cont. | 280 nm | |
| COP1 | AT2G32950.2 | 0.4 | 2.2 | genes |
| HYH | AT3G17609.4 | 2.5 | 5.9 | regulated by |
| | AT3G17609.3 | 0.0 | 5.3 | UVR8 |
| | AT3G17609.2 | 1.5 | 5.7 | |
| | AT3G17609.1 | −1.5 | 2.1 | |
| HY5 | AT5G11260.1 | 3.8 | 6.4 | |
| | AT5G11260.2 | −0.6 | 2.9 | |
| PAL1 * | AT2G37040.1 | 5.4 | 6.5 | Genes involved in |
| PAL2 * | AT3G53260.1 | 5.7 | 6.5 | phenylpropanoid |
| 4CL3 * | AT1G65060.1 | 0.2 | 2.0 | synthesis |
| | AT1G65060.2 | −4.2 | −2.7 | |
| 4CL2 * | AT3G21240.3 | −10.0 | −2.8 | |
| CHS * | AT5G13930.1 | 4.7 | 6.6 | Genes involved in |
| CHI1 * | AT3G55120.1 | 2.0 | 3.7 | flavonoid |
| FLS1 * | AT5G08640.1 | 1.0 | 4.2 | synthesis |
| | AT5G08640.2 | −3.3 | 0.3 | |
| CYP75B1 | AT5G07990.1 | 0.7 | 1.9 | |
| F3H * | AT3G51240.1 | 3.2 | 6.3 | |
| | AT3G51240.2 | −2.2 | 1.4 | |
| DFR * | AT5G42800.1 | 2.7 | 4.6 | |
| LDOX(ANS) * | AT4G22880.3 | 1.8 | 3.2 | |
| A3G2XYLT | AT5G54060.1 | −1.2 | 0.1 | Genes involved in |
| UGT75C1 | AT4G14090.1 | 0.0 | 1.5 | anthocyanin |
| MYB75 | AT1G56650.1 | −0.3 | 2.1 | synthesis |

Figure 8:
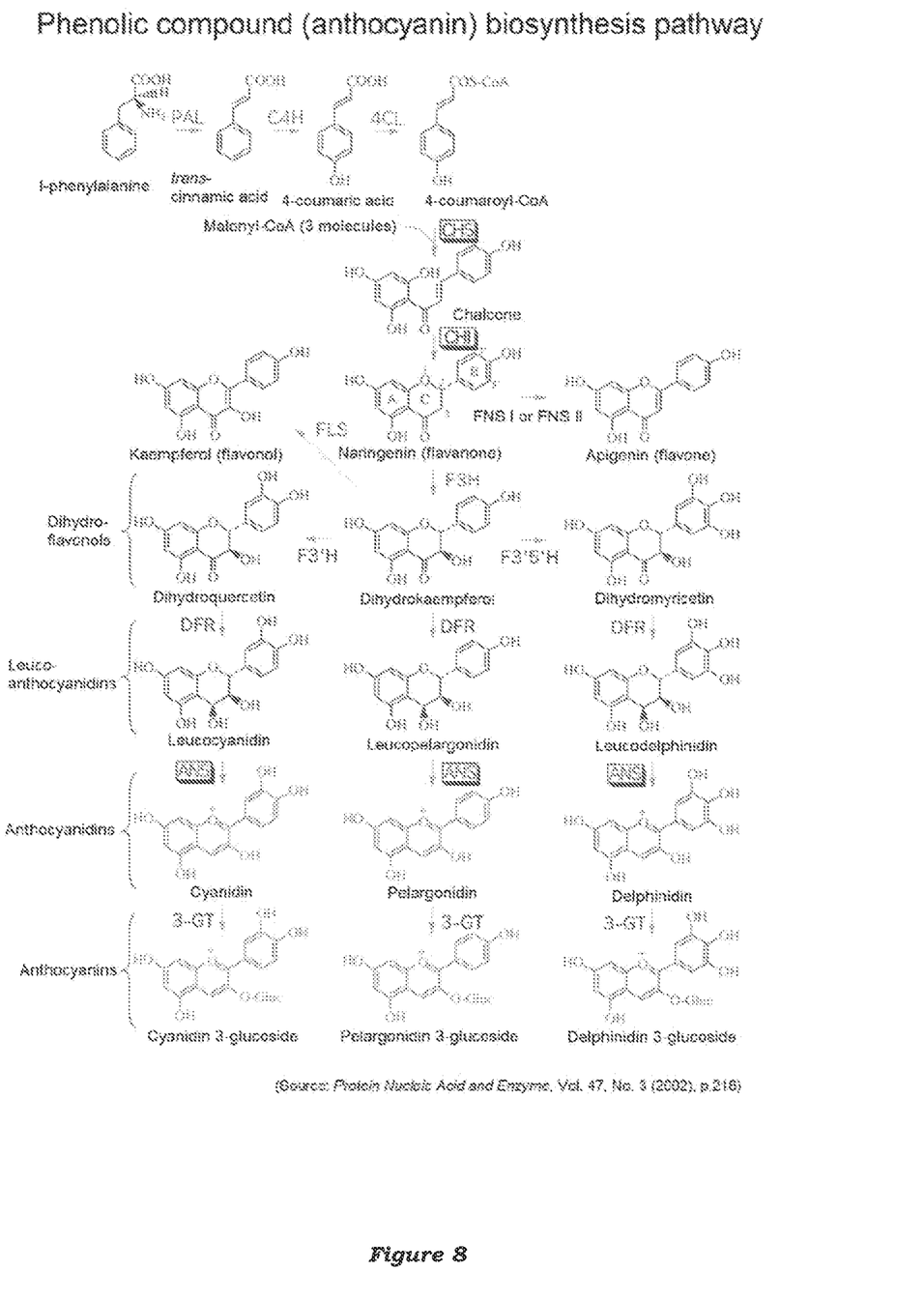
FIG. 8 illustrates biosynthetic pathways of phenolic compounds (anthocyanins) in plants.

In the table, genes marked with the asterisk "*" are those for the enzymes involved in biosynthetic pathways of phenol compounds (FIG. 8).

It is deduced that an increase in the amount of anthocyanins in plants irradiated with ultraviolet light at wavelengths of around 280 nm results from stimulation of UV-B photoreceptor-mediated signaling by the ultraviolet light irradiation through the activation (monomerization) of the photoreceptor UVR8 (Table 2), and thereby an increased expression of chalcone synthase, the rate-limiting enzyme in the shikimate pathway. Thus, it is believed that irradiation with ultraviolet light at wavelengths of around 280 nm results in increasing not only the amount of anthocyanins but the amount of phenolic compounds in general that are synthesized via the shikimate pathway, in plants (Experiments 3 and 4, FIGS. 5 and 6).

As the photoreceptor UVR8, the UV-B photoreceptor-mediated signaling system and the shikimate pathway are present not only in *A. thaliana* but commonly in the plant kingdom, it is believed that irradiation of ultraviolet light at wavelengths of around 280 nm results in increasing the amount of phenolic compounds in plants in general.

The invention claimed is:

1. A method for increasing an amount of a phenolic compound in a seedling, adult plant or harvested plant, the method comprising
    irradiating a seedling, adult plant or harvested plant, or part thereof, with ultraviolet light, wherein a fluence at wavelengths of 270 to 290 nm is 1500 to 50000 μmol/m² while a fluence at wavelengths of 310 to 400 nm is less than 50% of that at wavelengths of 270 to 290 nm,
    then placing the seedling, adult plant or harvested plant in a place where the photosynthetic photon flux density is 10 μmol/m²/s or less for 24 hours or more after the irradiation and
    subsequently obtaining or extracting the phenolic compound from the seedling, adult plant or harvested plant.

2. The method according to claim 1, wherein the fluence at wavelengths of 310 to 400 nm is less than 10% of that at wavelengths of 270 to 290 nm.

3. The method according to claim 1, wherein light at wavelengths of 270 to 290 nm is irradiated at a photon flux density of 1 to 5 μmol/m²/s.

4. The method according to claim 1, wherein a fluence at wavelengths of 200 to 260 nm is less than 20% of that at wavelengths of 270 to 290 nm.

5. The method according to claim 1, wherein a fluence at wavelengths of 200 nm or more and less than 270 nm is less than 10% of that at wavelengths of 270 to 290 nm.

6. The method according to claim 1, wherein the ultraviolet light has a wavelength spectrum with a peak wavelength at 280±5 nm and a half-width of 5 to 15 nm.

7. The method according to claim 1, wherein the ultraviolet light is emitted from a LED.

8. The method according to claim 1, wherein the seedling, adult plant or harvested plant is irradiated with ultraviolet light in the same place where the photosynthetic photon flux density is 10 μmol/m²/s or less.

9. The method according to claim 1, wherein the seedling, adult plant or harvested plant belongs to the family Brassicaceae, Berberidaceae, Theaceae, Fabaceae, Rutaceae or Vitaceae.

10. The method according to claim 1, wherein, after the irradiation, the seedling, adult plant or harvested plant, or part thereof, is disposed in a place where the photosynthetic photon flux density is 10 μmol/m²/s or less for 36 hours or more and less than 288 hours.

11. The method according to claim 1, wherein, after the irradiation, the seedling, adult plant or harvested plant, or part thereof, is disposed in a place where the photosynthetic photon flux density is 10 μmol/m²/s or less for 48 hours or more and less than 288 hours.

12. The method according to claim 1, wherein the seedling, adult plant or harvested plant is an adult plant or a harvested plant.

13. The method according to claim 1, wherein the seedling, adult plant or harvested plant is a seedling.

14. The method according to claim 1, wherein the seedling, adult plant or harvested plant is a harvested plant.

15. The method according to claim 1, wherein the seedling, adult plant or harvested plant is a harvested seedling or harvested adult plant.

16. A method for increasing an amount of a phenolic compound in a seedling, adult plant or harvested plant, the method comprising
    irradiating a seedling, adult plant or harvested plant, or part thereof, with ultraviolet light, wherein a fluence at wavelengths of 270 to 290 nm is 1500 to 50000 μmol/m² while a fluence at wavelengths of 300 to 400 nm is less than 50% of that at wavelengths of 270 to 290 nm, then placing the seedling, adult plant or harvested plant in a place where the photosynthetic photon flux density is 10 μmol/m²/s or less for 24 hours or more after the irradiation and subsequently obtaining or extracting the phenolic compound from the seedling, adult plant or harvested plant.

* * * * *